US006806049B1

(12) United States Patent
Maekawa et al.

(10) Patent No.: US 6,806,049 B1
(45) Date of Patent: Oct. 19, 2004

(54) METHOD FOR ANALYZING GENE EXPRESSION FREQUENCY

(75) Inventors: Takami Maekawa, Kawasaki (JP); Akira Mitsui, Kawasaki (JP); Masayo Date, Kawasaki (JP); Hisao Fukuda, Kawasaki (JP); Yoshiyuki Takahara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/926,028
(22) PCT Filed: Feb. 17, 2000
(86) PCT No.: PCT/JP00/00902

§ 371 (c)(1),
(2), (4) Date: Aug. 16, 2001

(87) PCT Pub. No.: WO00/49143

PCT Pub. Date: Aug. 24, 2000

(30) Foreign Application Priority Data

Feb. 17, 1999 (JP) ............................... 11-38538

(51) Int. Cl.[7] ............................ C12Q 1/68; C12P 19/34; C07H 21/02; C07H 21/04
(52) U.S. Cl. ........................ 435/6; 435/91.2; 536/23.5; 536/24.31; 536/24.33
(58) Field of Search .......................... 435/6, 91.1, 91.2; 536/23.1, 23.5, 24.31, 24.33

(56) References Cited

U.S. PATENT DOCUMENTS 5,695,937 A 12/1997 Kinzler et al.
5,866,330 A * 2/1999 Kinzler et al. ................. 435/6
6,136,537 A * 10/2000 Macevicz ....................... 435/6

FOREIGN PATENT DOCUMENTS

WO WO 97/10363 3/1997

OTHER PUBLICATIONS

Okubo et al. DNA Sequence (1991) vol. 2, pp. 137–144.*
S. Giguere, et al., Vet. Immunol. Immunopathol., vol. 67, No. 1, pp. 1–15, "Quantitation of Equine Cytokine mRNA Expression by Reverse Transcription–Competitive Polymerase Chain Reaction", Jan. 4, 1999.
G.J. Czarnota, et al., Micron, vol. 28, No. 6, pp. 419–431, "High Resolution Microanalysis and Three–Dimensional Nucleosome Structure Associated with Transcribing Chromatin", Dec. 1997.
V. Berangere, et al., Proc. Natl. Acad. Scl. USA, vol. 96, No. 26, pp. 15286–15291, "Serial Microanalysis of Renal Transcriptomes", Dec. 21, 1999.
Kawamoto et al., "Expression profiles of active genes in human and mouse livers" Gene. Netherlands, Sep. 26, 1996, vol. 174, No. 1, pp. 151–158.

* cited by examiner

Primary Examiner—Jeffrey Fredman
Assistant Examiner—Sally Sakelaris
(74) Attorney, Agent, or Firm—Oblon, Spivak, McClelland, Maier & Neustadt, P.C.

(57) ABSTRACT

In gene expression frequency analysis, a vector primer to which each cDNA is ligated is formed by synthesizing the cDNA from each mRNA using by a vector primer having a poly(T) sequence; each cDNA sequence is converted to a tag on the vector primer; a concatemer is formed by ligating the obtained tags via a sequence that enables recognition of ends of the tags; and the nucleotide sequence of the concatemer is analyzed.

20 Claims, 5 Drawing Sheets

METHOD FOR ANALYZING GENE EXPRESSION FREQUENCY

TECHNICAL FIELD

The present invention relates to a method for analyzing expression frequencies of genes. More precisely, the present invention relates to a method that enables analysis of types and amounts of mRNA expressed from all of genes coding for proteins in a cell even with a small amount of biosample in order to elucidate dynamic change of gene expression.

BACKGROUND ART

The total number of genes on the genome coding for proteins is expected to be about 100,000 for human. As for yeast, of which total genomic structure have already been elucidated, the number of genes coding for proteins are estimated to be about 5000.

In recent years, public gene databanks have been established mainly in Europe, the United States and Japan. An enormous amount of gene information has been registered at such databanks from all over the world, and further information is newly coming together into the databanks every day. The human genome project is currently being pursued in a worldwide scale aiming at elucidating the total genes of human genome by the year of 2005, and the gene information obtained in that project is also being registered at the databanks. By inquiring to such databanks about a certain gene sequence, one can know if any gene having the same sequence as, or analogous sequence to the gene sequence has already been registered or not and, if registered, information concerning the sequence including designation and function of the gene, related references and so forth. Such a search is called homology search. There are several kinds of software for performing homology search. However, when a large number of samples must be searched for, BLAST is usually used, of which searching time is short.

Usually, all of genes contained in a cell are not necessarily transcribed into mRNA so as to produce proteins from mRNA, and it is estimated for human that about 15000 genes are expressed in one cell. Thus, in a cell, many kinds of genomic genes are expressed, and a corresponding number of types of messenger RNA (henceforth referred to as "mRNA") are produced. However, types and amounts of expressed genes (also referred to as "genetic expression frequency information" hereinafter) may vary depending on the types and conditions of cells. For example, when a blood stem cell differentiates into a lymphocyte precursor cell, pre-B cell, B cell, and then activated B cell, each cell shows entirely different gene expression, although there are also genes that are commonly expressed in them.

Measurement of such genetic expression frequency information as described above is called genetic expression profile analysis. Substances responsible for cellular life activities are mainly proteins, and it is important to analyze types and amounts of proteins translated from mRNAs as the genetic expression analysis. However, it is technically difficult under a current situation to obtain profiles for the total proteins. On the other hand, measurement of total types of mRNA has already become possible.

The method reported for the first time as the genetic expression profile analysis method is the Body Map method (Gene, 174, 151–158 (1996)). The outline of the Body Map method is as follows. A poly(T) sequence on a vector is annealed to a poly(A) tail at the 3' end of each mRNA, and a cDNA is synthesized by using the vector poly(T) sequence as a primer. Further, the cDNA is digested with a restriction enzyme MboI. Since one of MboI site exists in every 300 base pairs of cDNA in average, the cDNA on the vector is digested into a length of 300 base pairs in average. At this time, a cDNA fragment nearest the poly(A) tail remains ligated to the vector. The vector having this cDNA fragment is each cyclized and introduced into *Escherichia coli* to prepare a cDNA library. About 1000 clones are arbitrarily selected from the library, and the nucleotide sequence for 300 base pairs in average of each clone is determined. The clones were divided into groups of clones having the same sequence, and type and occurring frequency of each sequence are calculated to obtain genetic expression profile. Homology search (BLAST search) is performed in a databank for each cDNA sequence, and clones containing genes having the same sequence as known genes are given the names of the genes. When the sequence is not registered at the databank, it is considered that no gene corresponding to the sequence exists.

In order to perform homology search by the BLAST search, information for at least 11 base pairs is required. The types of sequences consisting of 10 nucleotides are about 1,000,000, and this number is far beyond the number of gene types of which existence is expected in human, i.e., 100,000. That is, if there is information for 11 base pairs, a gene having the sequence can be identified and thus the genetic expression profile analysis is possible. Therefore, if, aiming at increasing the efficiency of the genetic expression profile analysis by Body Map which requires much sequencing, cDNA fragments of about 300 base pairs used in Body Map are further made into short fragments of 11 base pairs or more (called "tag"), many of these fragments are ligated and inserted into a vector to prepare a library of ligated tags, about 1000 clones are arbitrarily selected as in Body Map, and DNA sequences of the ligated tags are determined, it is expected that more genetic expression information can be obtained with the same labor compared with Body Map. Each tag represents a gene sequence, and occurring frequency of the tag indicates expression frequency of the gene. Since the length of DNA sequence that can be determined by once of sequencing is usually about 600 base pairs, DNA sequences of about 50 tags at most can be determined by once of sequencing. That is, it becomes possible to perform the genetic expression profile analysis with efficiency about 50 times higher than that of the Body Map method.

As a method for genetic expression profile analysis based on the aforementioned concept, there is the method of serial analysis of gene expression (SAGE, U.S. Pat. Nos. 5,695,937 and 5,866,330, European Patent Publication No. 0761822 A). In SAGE, cDNA is produced by using a poly(T) of which 3' end is bonded with biotin as a primer, the cDNA is digested with a restriction enzyme such as MboI (called an "anchoring enzyme") as in Body Map, cDNA fragments containing the 3' end to which biotin is bonded are adsorbed on avidin beads, the beads are divided into two of portions, and two kinds of linkers (A or B) are each ligated to the cDNA fragments (about 13 bp) adsorbed on either of the two portions of the beads. Each linker contains a site for a Class II restriction enzyme such as BsmFI (called a "tagging enzyme"). Each cDNA fragment is excised from the beads with the tagging enzyme, the excised end is blunt-ended, and the tags ligated to the linker A and the linker B are connected. The product of the connection is called a "ditagt". The ditag is amplified by PCR using primers that recognize the linker A and the linker B. A large number of amplified ditags are ligated, inserted into a vector, and sequenced. About 50 tag sequences can be obtained by once of sequencing. By calculation based on this tag sequence information, genetic expression frequencies are provided.

Further, as other methods for analyzing expression frequencies of genes, there are the gene chip method and the gene microarray method. In both of the methods, there are used gene fragments adhered in array to a suitable plate (usually slide glass) at an extremely high density (about 10 fragments/mm$^2$ or more). The gene fragments on this chip are hybridized with fluorescence-labeled mRNAs to determine types and amounts of mRNAs.

As described above, several methods have been developed for analyzing expression frequencies of genes, and fair results have been obtained. Currently, the SAGE method is the most effective means for measuring expression frequencies of the total genes of all eukaryotic organisms. However, when this method was actually practiced, it encountered many problems, and the SAGE method could not be reproduced in most of research facilities. That is, the techniques required for the SAGE method are complicated and they can be performed only by specially trained persons. Further, about 1 μg of mRNA is required for the measurement, and therefore it is substantially impossible to perform the measurement with a sample that can be obtained in a small amount, for example, a clinical biopsy material, or to measure difference of genetic expression in micro tissue portions. Furthermore, the method theoretically causes considerable measurement errors.

In the SAGE method, it is extremely important to accurately determine a sequence of the tag. This is because the tag is short (about 13 bp) and therefore, if even only one of nucleotides is erroneously determined, it may be determined to be a different sequence even though it is the same sequence, or a different sequence may be determined to be the same sequence. However, such an erroneous determination is likely to occur in the SAGE method. This is because, in the SAGE method, two tags are connected to form a ditag and the border between the tags becomes indefinite. The tag is a short gene fragment excised by a restriction enzyme such as BsmFI and FokI. However, cleavage sites of these enzymes are not always stable, and the lengths of the excised tags are diversified. Thus, if the tags are connected to form a ditag in the state that tags of different lengths are intermingled, it becomes indefinite from which tag nucleotides at the ligation site of the tags have been derived. As a result, it becomes impossible to obtain a correct sequence of the tag. Thus, the SAGE method suffers from a theoretically inevitable drawback. Furthermore, the SAGE method involves an operation of collecting DNA using avidin and biotin beads. However, it is in fact extremely difficult to collect DNA by using avidin and biotin beads without inviting contamination, and it is extremely difficult to obtain correct data by operating according to the protocol as it is. Moreover, the SAGE method requires a large amount of mRNA in order to obtain data. Therefore, in a case of a sample of which amount is limited, for example, clinical samples, a sufficient amount of mRNA cannot be obtained and thus the SAGE method cannot be performed.

Furthermore, in the gene chip method and the gene microarray method, the measurement can be performed only for a gene of which structure is known, unlike the Body Map method or the SAGE method. Therefore, under the current situation, expression frequencies of total genes of all organisms cannot be measured.

Currently, the SAGE method is the most effective means for measuring expression frequencies of the total genes of all eukaryotic organisms. However, when this method was actually practiced, it encountered many problems, and the SAGE method could not be reproduced in most of research facilities. The drawbacks of the SAGE method are as follows: (1) the techniques required for the method are complicated and they can be performed only by specially trained persons; (2) about 1 μg of mRNA is required for the measurement, and therefore it is substantially impossible to perform the measurement with a sample that can be obtained in a small amount, for example, a clinical biopsy material, and it is similarly impossible to measure difference of genetic expression in micro tissue portions; and (3) the method theoretically causes considerable measurement errors because a ditag is measured.

DISCLOSURE OF THE INVENTION

The present invention was accomplished in view of the aforementioned current situation, and an object thereof is to provide a method that can be easily performed by ordinary researchers and enables accurate genetic expression frequency analysis with a micro amount of a specimen.

The inventors of the present invention assiduously studied in order to achieve the aforementioned object. As a result, they found that expression frequencies of genes could be efficiently analyzed with high precision by synthesizing each cDNA from each mRNA using a vector primer having a poly(T) sequence, converting each cDNA sequence to a tag on the vector, forming a concatemer by ligating the obtained tags via a sequence that enables recognition of ends of the tags, and analyzing a nucleotide sequence of the concatemer, and thus accomplished the method of the present invention designated as "MAGE (Micro-analysis of Gene Expression)".

That is, the present invention provides the followings.

(1) A method for analyzing expression frequencies of genes, which comprises the following steps:

(a) a step of forming a vector primer to which each cDNA is ligated, by annealing the vector primer with each mRNA derived from a cell of which expression frequencies of genes is to be analyzed, and synthesizing the cDNA, said vector primer comprising a linear plasmid vector having a single-stranded poly(T) sequence at one 3' end, a recognition sequence for a first restriction enzyme in an inner position from the poly(T) sequence, a recognition sequence for a second restriction enzyme near the other end, and a recognition sequence for a type IIS restriction enzyme in an inner position from the recognition sequence for the second restriction enzyme, (b) a step of digesting the vector primer to which the cDNA is ligated, with the second restriction enzyme and a third restriction enzyme that does not digest the vector primer and forms a digested end of the same shape as a digested end obtained with the second restriction enzyme, to excise an upstream region of the cDNA, and cyclizing the vector primer, (c) a step of digesting the cyclized vector primer with the first restriction enzyme and the type IIS restriction enzyme to excise a downstream region of the cDNA so that a tag consisting of a part of the cDNA is left, and cyclizing the vector primer again, (d) a step of performing polymerase chain reaction (PCR) by using the vector primer as a template and oligonucleotides having nucleotide sequences corresponding to respective flanking regions of the both sides of the tag contained in the vector primer as primers to amplify the tag, (e) a step of ligating the amplification products to form a concatemer of the tags, and (f) a step of determining the nucleotide sequence of the concatemer and investigating types and frequencies of tags occurring in the nucleotide sequence.

(2) The method according to (1), wherein the ligation reaction in the step (e) is performed in the presence of an adaptor having one end of the same shape as an end of the tag to arrange the adaptor at each end of the concatemer, and the concatemer is amplified by performing PCR using an oligonucleotide having a sequence corresponding to the sequence of the adaptor as a primer.

(3) The method according to (1) or (2), wherein, after the step (e), the concatemer is cloned in a cloning vector for nucleotide sequencing, and then the nucleotide sequence of the concatemer is determined.

(4) The method according to any one of (1) to (3), wherein the recognition sequence for the third restriction enzyme consists of four nucleotides.

(5) The method according to any one of (1) to (4), wherein the vector primer has a recognition sequence for a fourth restriction enzyme of which digestion point is in the same position as or an inner position from the digestion point of the recognition sequence for the second restriction enzyme, which is not excised from the vector primer by the digestion with the type IIS restriction enzyme;

the primer for the downstream side of the tag among the primers used in the step (d) has a recognition sequence for a fifth restriction enzyme that forms an end of the same shape as the end digested with the fourth restriction enzyme; and the concatemer is formed after the amplified primers are digested with the fourth restriction enzyme and the fifth restriction enzyme.

(6) The method according to (5), wherein the vector primer has a nucleotide sequence different from the recognition sequence for the fifth restriction enzyme by one nucleotide in an inner position from the recognition sequence for the first restriction enzyme, and the nucleotide sequence different by one nucleotide is converted to the recognition sequence for the fifth restriction enzyme by PCR using the primer for the downstream side of the tag.

(7) The method according to (6), wherein the third, fourth and fifth restriction enzymes are identical to one another.

(8) The method according to any one of (1) to (7), wherein the vector primer is formed by ligating a linear plasmid obtained by digesting a plasmid having a multicloning site at two sites in the multicloning site, and a partially double-stranded DNA having an end of the same shape as one end of the linear plasmid and a single-stranded poly(T) sequence.

BRIEF EXPLANATION OF THE DRAWINGS

In FIG. 2C, a partially double-stranded DNA having a single-stranded poly(T) sequence is introduced having the following DNA sequences (all listed 5' to 3'): CGGAGTTTAAACGGATTGGAGCCAGC (SEQ ID NO: 24) GCTCCAATCCGTTTAAACTCCGTTTTTTTTTTTTTTTTTTTTTTTTTTTTTTTTT (SEQ ID NO: 25). In FIG. 2D, ligation results in the following DNA sequences (all listed 5' to 3'): CGGAGTTTAAACGGATTGGAGCCAGCATGGAAGCTT (SEQ ID NO: 26) AAGCTTCCATGCTGGCTCCAATCCGTTTAAACTCCGTTTTTTTTTTTTTTTTTTTTTTTTTTTTTTT (SEQ ID NO: 27).

In FIG. 3E, the sequence (5' to 3') ------------------------------------------------- AAAAAAAAAAAAAAAAAAAAAAAA (SEQ ID NO: 28) is introduced to AAGCTTCCATGCTGGCTCCAATCCGTTTAAACTCCGTTTTTTTTTTTTTTTTTTTTTTTTTTTT (5' to 3' sequence; SEQ ID NO: 29). The resulting representative synthesized DNA in FIG. 3F has the sequence (5' to 3'): NNNNNNNNNNNNNNNNNNNNNNNNNNNNNNNNNNNNNNNNNNNNAAAA AAAAAAAAAAAAAAACGGAGTTTAAACGCGATTGGAGCCAGCTGGAAGCTT (plus strand; SEQ ID NO: 30) and AAGCTTCCATGCTGGCTCCAATCCGTTTTTTTTTTTTTTTTTTTN NNNNNNNNNNNNNNNNNNNNNNNNNNNNNNNN NNNNNNNNN (minus) strand; SEQ ID NO: 31).

In FIG. 4I, the represented DNA sequence has the following sequence (5' to 3'): GAATTCGTGCAGATCNNNNNNNNNNNNNNNNNNNNNNNNNAAAAA AAA AAAAAAACGGAGTTTAAACGGATTGGAGCCAGCATGGAAGCTT (plus strand; SEQ ID NO: 32) and AAGCTTCCATGCTGGCTCCAATCCGTTTAAACTCCGTTTTTTTTTTTTTTTTNNNNN NNNNNNNNNNNNNNNNNNNNNNNNNGATCTGCACGAATTC (plus strand; SEQ ID NO: 33). Following BsgI and PmeI treatment, FIG. 4J shows the following DNA fragments (all listed 5' to 3'): GAATTCGTGCAGATCNNNNNNNNNNNN (SEQ ID NO: 34) NNNNNNNNNNNNNNNNAAAAAAAAAAAAAAACGGAGTTT (SEQ ID NO: 35) AAACGGATTGGAGCCAGCATGGAAGCTT (SEQ ID NO: 36) NNNNNNNNNNNGATCTGCACGAATTC (SEQ ID NO: 37) AAACTCCGTTTTTTTTTTTTTTT-NNNNNNNNNNNNNNNNNNNN (SEQ ID NO: 38) AAGCTTCCATGCTGGCTCCAATCCGTTT (SEQ ID NO: 39). Following 1) blunting of ends and 2) ligation and cyclization FIG. 4K provides the following exemplary sequence (5' to 3'): GAATTCGTGCAGATCNNNNNNNNNNAAACGGATTGGAGCCAGCATGGAAGCTT (plus strand; SEQ ID NO: 40) and (bottom strand; SEQ ID NO: 41). In FIG. 4L, a exemplary PCR amplification product is provided with the following sequence (5' to 3'): GATCNNNNNNNNNNAAACGGATC (plus strand; SEQ ID NO: 42) and GATCCGTTTNNNNNNNNNNGATC (minus strand; SEQ ID NO: 43).

BEST MODE FOR CARRYING OUT THE INVENTION

The method of the present invention comprises the aforementioned steps (a) to (f). Hereafter, each step will be explained.

<1> Step (a)

In the first step, a vector primer comprising a linear plasmid vector having a single-stranded poly(T) sequence at one 3' end, a recognition sequence for a first restriction enzyme in an inner position from the poly(T) sequence, a recognition sequence for a second restriction enzyme near the other end, and a recognition sequence for a type IIS restriction enzyme in an inner position from the recognition sequence for the second restriction enzyme is used (also referred to as a "the vector primer for reverse transcription" hereinafter). The type IIS restriction enzyme means a restriction enzyme that cleaves a specific position remote from a sequence recognized by the restriction enzyme.

Figure 1:
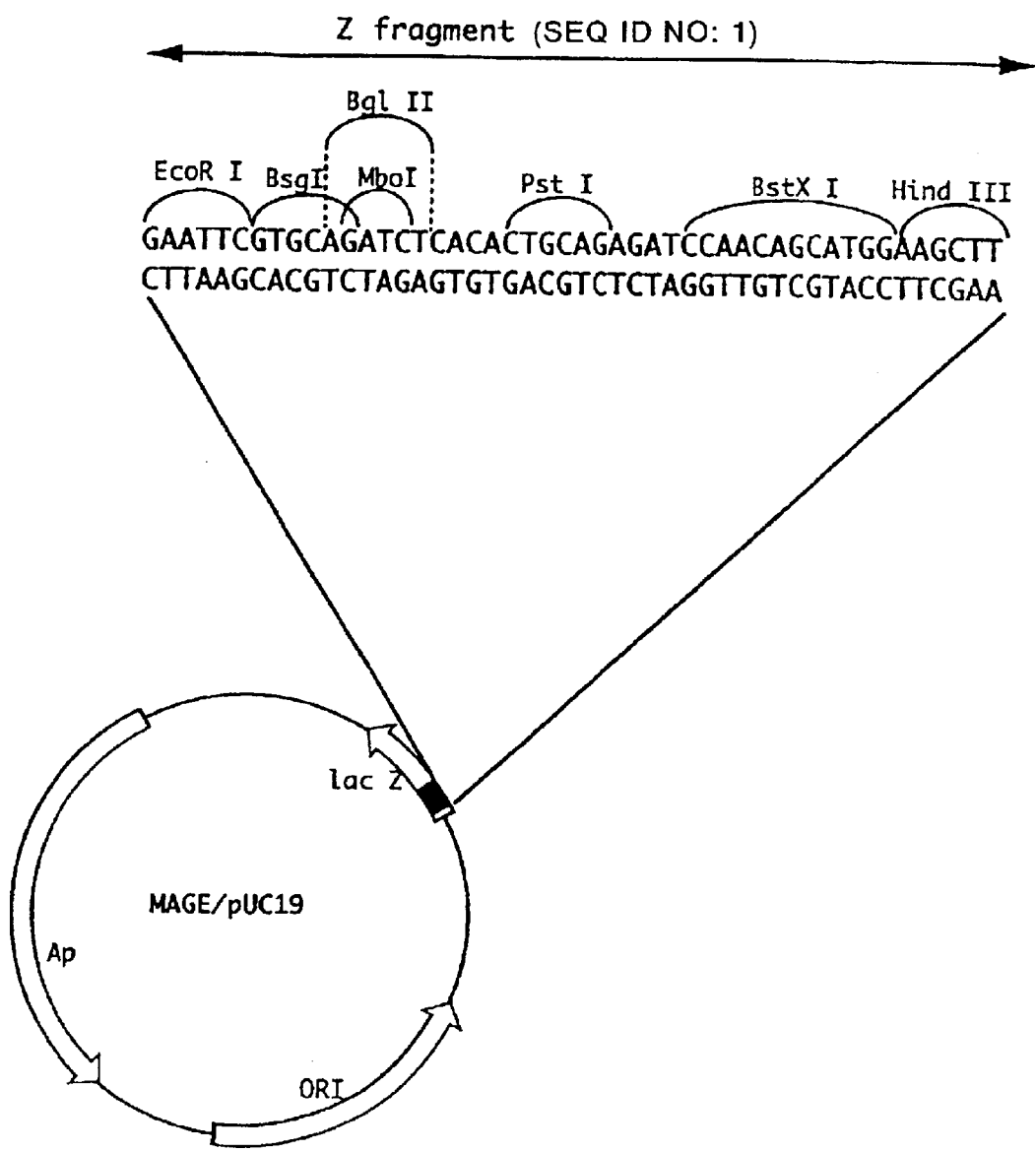
FIG. 1 shows an exemplary structure of plasmid DNA for producing a vector primer (MAGE/pUC19). The structure of the MAGE/pUC19 is shown having a multiple cloning sequence of GATTCGTGCAGATCTCACACTGCAGAGATCCAACAGCATGGAAGCTT (plus strand; SEQ ID NO: 1) and the corresponding minus strand having a sequence (5' to 3') of AAGCTTCCATGCTGTTGGATCTCTGCAGTGTGAGATCTGCACGAATTC (SEQ ID NO: 17). In this, and subsequent, figure(s), the term "plus strand" represents the top sequence, which is shown in the figure in 5' to 3' orientation, and the term "minus strand" represents the bottom sequence, which is shown in the figure in 3' to 5' orientation.
Figure 2:
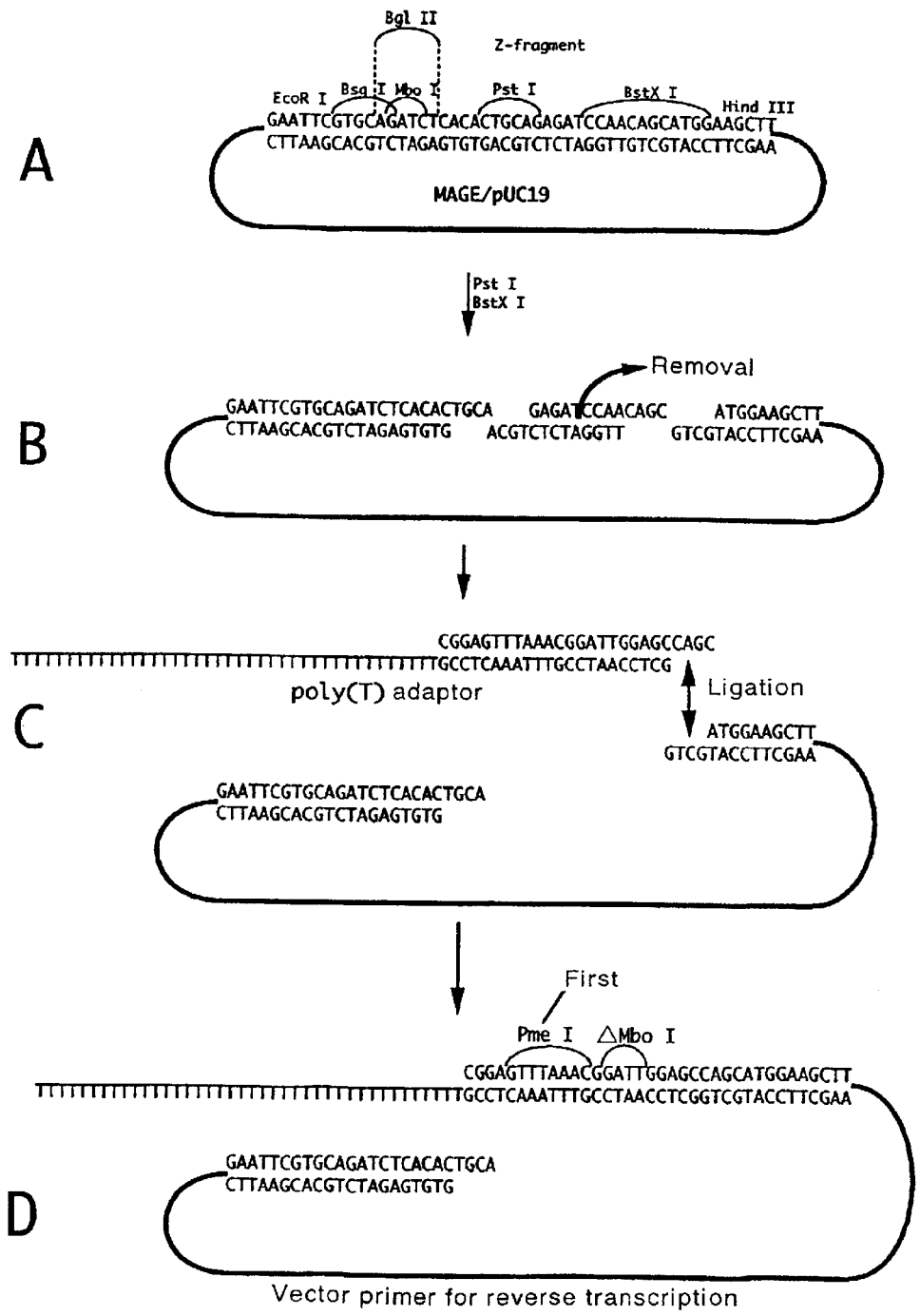
FIG. 2 shows an exemplary structure of a vector primer and a construction process therefor. PstI and BstXI cleavage results in the following DNA fragments (all listed 5' to 3') shown in FIG. 2B: GAATTCGTGCAGATCTCACACTGCA (SEQ ID NO: 18) GAGATCCAACAGC (SEQ ID NO: 19) ATGGAAGCTT (SEQ ID NO: 20) GTGTGAGATCTGCACGAATTC (SEQ ID NO: 21) TTGGATCTCTGCA (SEQ ID NO: 22) AAGCTTCCATGCTG (SEQ ID NO: 23).

An exemplary structure of the vector primer is shown in FIG. 2, D. This vector primer can be prepared by, for example, ligating a linear plasmid obtained by digesting a plasmid having a multicloning site at two sites in the multicloning site, and a partially double-stranded DNA having an end of the same shape as one end of the linear plasmid and a single-stranded poly(T) sequence. The structure of MAGE/pUC19 is shown in FIG. 1 as an example of the plasmid having a multicloning site. This primer comprises pUC19, which is a known cloning vector, as a basic structure, and a sequence containing various restriction enzyme recognition sites (referred to as "Z fragment", sequence is shown in SEQ ID NO: 1) is inserted between the EcoRI and HindIII restriction enzyme sites of the multicloning site thereof.

In the following specific example, explanation will be made for an example that utilizes MAGE/pUC19 prepared by using an *Escherichia coli* host having Dam methylation system, for example, JM109 strain etc. However, it is not essential for the present invention. Further, the vector used as the basic structure is not limited to pUC19, and various other vectors such as pUC18, pBR322, pHSG299, pHSG298, pHSG399, pHSG398, RSF1010, pMW119, pMW118, pMW219 and pMW218 can be used. In addition, the host of the vector is not particularly limited, so long as it is one for which ordinary genetic recombination techniques such as transformation and recovery of vectors from the host can be used. However, *Escherichia coli* is usually used.

An example utilizing MAGE/pUC19 as the plasmid having a multicloning site will be explained hereafter. However, the present invention is not limited to this example.

First, MAGE/pUC19 vector (FIG. 2, A) is digested with restriction enzymes BstXI and PstI, and the excised small fragment is removed (FIG. 2, B). Then, a partially double-stranded DNA having a single-stranded poly(T) sequence (poly(T) adaptor shown in FIG. 2, C) is ligated to the BstXI-digested end. This provides a vector primer (or a vector primer for reverse transcription) in which the single-stranded poly(T) protruding from one end of the MAGE/pUC19 vector (FIG. 2, D). In this vector primer, the first restriction enzyme is PmeI, the second restriction enzyme is BglII, and the type IIS restriction enzyme is BsgI.

The recognition sequence for the second restriction enzyme BglII contains an overlapping MboI recognition sequence, and therefore if the BglII end is ligated to the MboI end, it can be digested with MboI. Further, in this example, the vector primer is designed to contain a nucleotide sequence (AMboI of FIG. 3, E) that is different from the fourth restriction enzyme (MboI) recognition sequence by one nucleotide in a further inner position from the first restriction enzyme (PmeI) recognition sequence. This ΔMboI and the first restriction enzyme recognition sequence of the vector primer are derived from the poly(T) adaptor.

The first restriction enzyme and the second restriction enzyme are not particularly limited, so long as they digest the vector primer at one position. Further, the type IIS restriction enzyme and its recognition sequence-existing position are not particularly restricted, so long as it does not excise the fourth restriction enzyme site from the vector primer, and it digests the upstream region of the cDNA so that a part of the cDNA is left on the vector primer. Specifically, it may be, for example, BsmFI etc., in addition to the aforementioned BsgI.

Further, the length of the poly(T) sequence may be a length that enables annealing with the poly(A) sequence of mRNA, and it is usually about 10–50 nucleotides.

Figure 3:
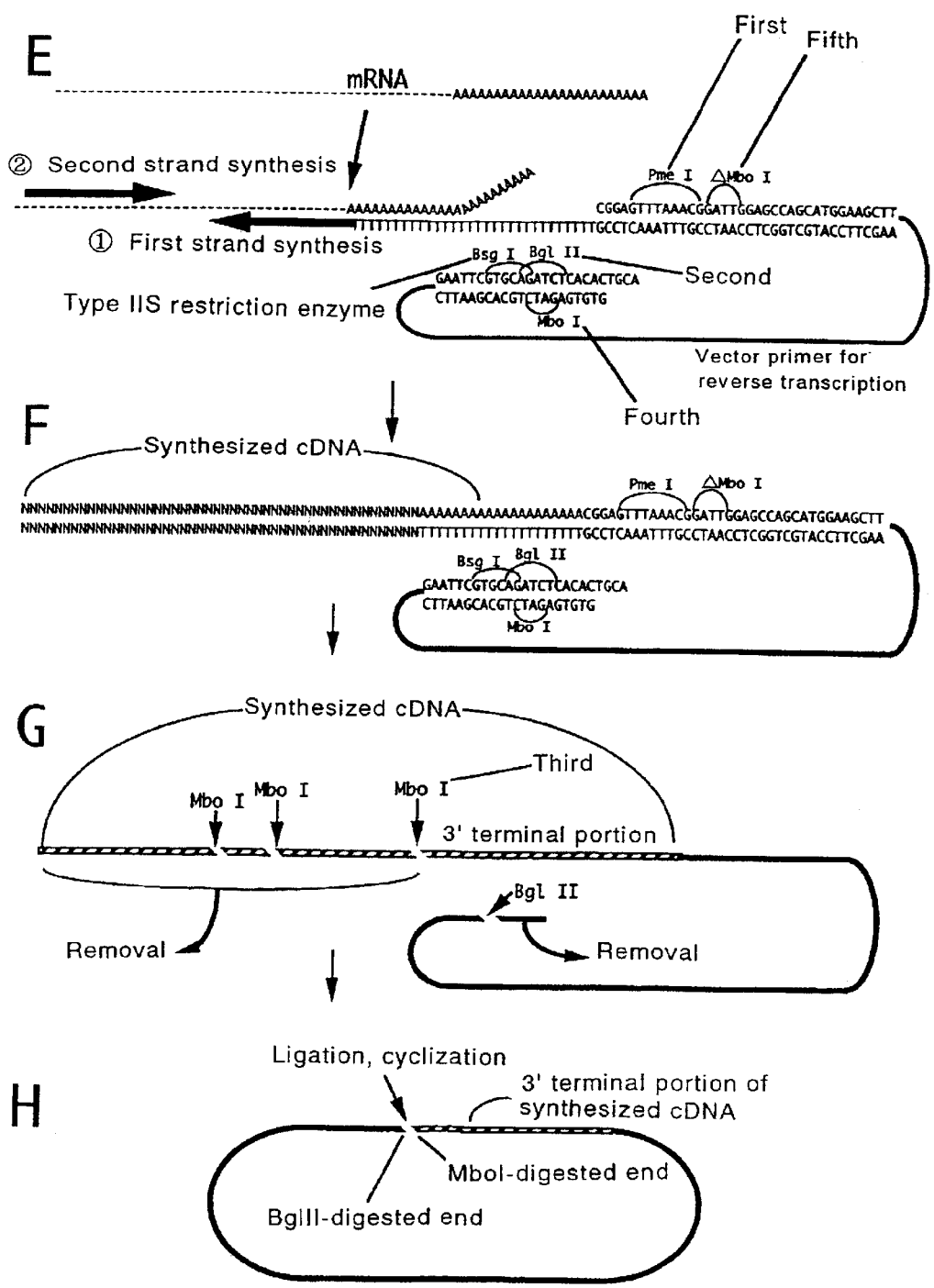
FIG. 3 schematically shows the steps (a) and (b) of the method of the present invention.

Such a vector primer as mentioned above and mRNA derived from a cell for which expression frequencies of genes are to be analyzed are annealed. When a reverse transcription reaction is performed in that state, the poly(T) serves as a primer and cDNA synthesis is initiated (FIG. 3, E). Then, the second strand can be synthesized by using the synthesized first strand of cDNA as a template to synthesize a double-stranded cDNA (FIG. 3, F). While a large number of vector cDNA-ligated primer molecules (cDNA-MAGE/pUC19) can be produced from a large number of mRNA molecules, FIG. 3, F represents one of typical example thereof.

The mRNA is extracted from a cell for which expression frequencies of genes are to be analyzed. Any cell can be used as the cell for which expression frequencies are to be analyzed without any particular limitation, so long as it is a cell in which 3' end of mRNA has the poly(A) structure, and it may be a tissue cell of an animal or a plant, a cell of a microorganism such as yeast. Further, mRNA of a prokaryote does not have the poly(A) structure at the 3' end and therefore it cannot be annealed as it is to the poly(T) of the vector primer. However, by enzymatically adding a poly(A) structure to the mRNA, the method of the present invention can be performed in a manner similar to that for mRNA of an eukaryotic organism.

Operations such as preparation of mRNA, cDNA synthesis, synthesis of oligonucleotide, reaction with a restriction enzyme, ligation reaction, polymerase chain reaction (PCR), and transformation can be performed in the same manner as methods for preparing mRNA used for usual cDNA cloning (see, for example, Sambrook J., Fritsch, E. F., and Maniatis, T., "Molecular Cloning A Laboratory Manual, Second Edition", Cold Spring Harbor Laboratory Press (1989) etc.).

<2> Step (b)

Then, the vector primer to which cDNA is ligated, obtained as described above, is digested with the second restriction enzyme and a third restriction enzyme that does not digest the vector primer and forms a digested end of the same shape as a digested end obtained with the second restriction enzyme, to excise an upstream region of the cDNA, and the vector primer is cyclized. The cyclized vector primer can be amplified by introducing it into a suitable host, culturing the obtained transformant, and collecting a plasmid. As will be similarly applied to cyclized vector primers used in the subsequent steps, when the restriction enzyme site for cleaving the obtained vector primer cannot be digested due to Dam methylation, a host that does not have the modification system is used.

As the third restriction enzyme, an enzyme recognizing four nucleotides is preferred. If an enzyme recognizing six nucleotides is used, such a restriction enzyme site may not exist in the cDNA sequence. Further, if the sequence of cDNA left on the vector primer is long, the tag obtained by the subsequent procedures will become far from the poly(A) sequence of mRNA. In such a case, since the expression information of genes in a database (EST: expressed sequence tag) is usually for parts of the 3' end side of mRNA, the target sequence may not be retrieved even if tag sequences are searched. Examples of restriction enzyme suitable for the present invention, which recognize four nucleotides, include MboI, TaiI and so forth.

Hereafter, an example utilizing MboI as the third restriction enzyme will be explained. First, the cDNA-ligated vector primer (cDNA-MAGE/pUC19) is digested with restriction enzymes BglII and MboI (FIG. 3, G). Since MAGE/pUC19 have been Dam-methylated at this time, it is not digested with MboI, and only the MboI site newly synthesized in the cDNA by the reverse transcription is digested. FIG. 3, G shows a temporary example where the cDNA contains three of MboI sites. As for the cDNA, a downstream region from the poly(A) tail to the first MboI site toward the upstream region remains ligated to the MAGE/pUC19 vector primer, and the other portion, i.e., the upstream region of the cDNA is excised and removed by the MboI digestion. As for MAGE/pUC19, it is digested with BglII at only one position. The end portions digested with MboI and BglII are in the same shape, and they can be ligated by a ligation reaction. Therefore, the cDNA-MAGE/pUC19 is cyclized by a self-ligation reaction via these ends (FIG. 3, H).

<3> Step (c)

The vector primer cyclized in the step (b) is digested with the first restriction enzyme and the type IIS restriction enzyme to excise the downstream region of the cDNA, so that a tag consisting of a part of the cDNA is left, and the vector primer is cyclized again.

Figure 4:
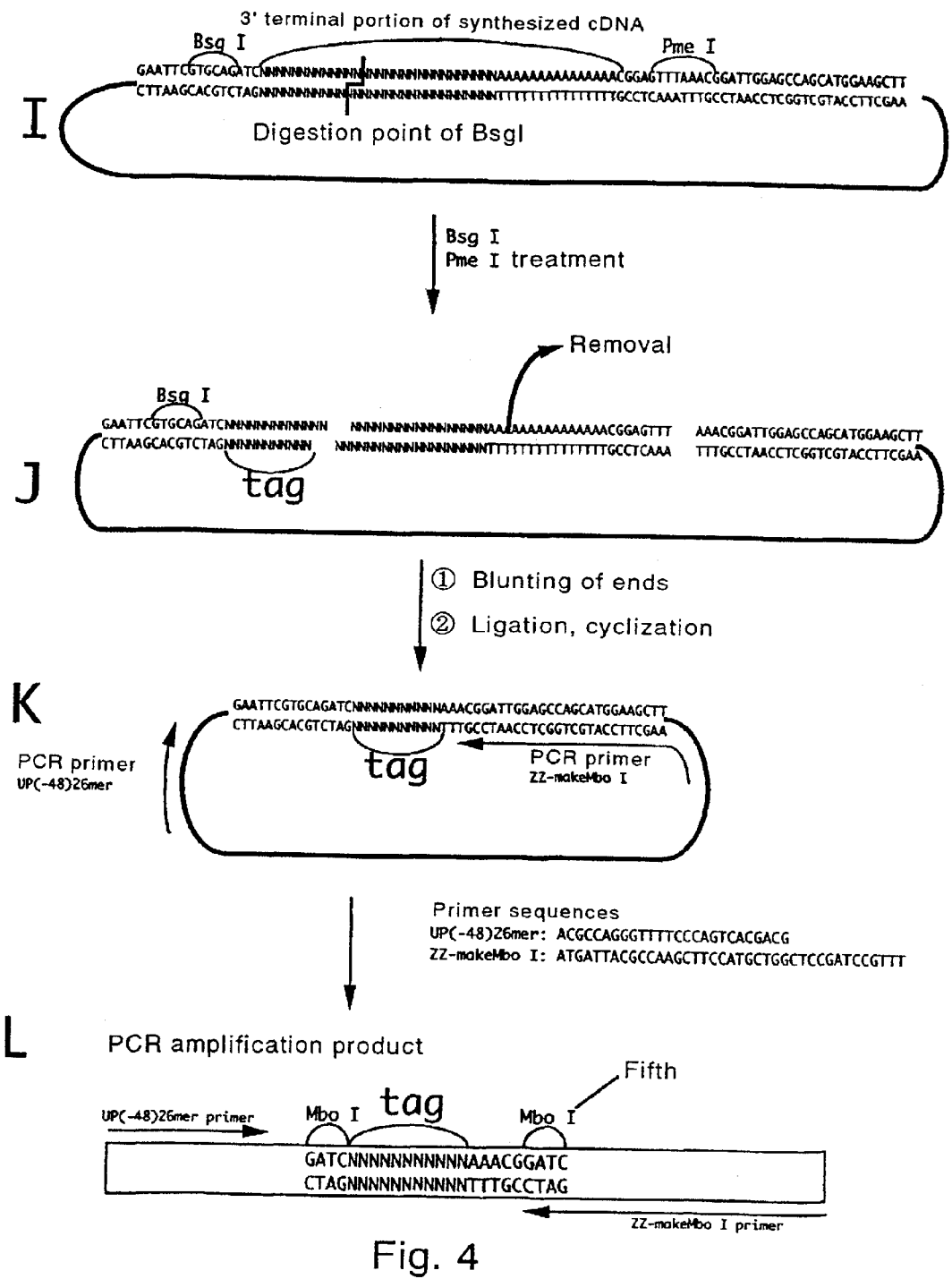
FIG. 4 schematically shows the steps (c) and (d) of the method of the present invention.

Specifically, the cyclized cDNA-MAGE/pUC19 is digested with restriction enzymes BsgI and PmeI (FIG. 4, I). After digestion with these restriction enzymes, only about 13 nucleotides farthest from the poly(A) tail of the 3' end portion of the cDNA remain on the vector primer. This sequence of cDNA consisting of about 13 nucleotides is called tag (shown in FIG. 4, J as "tag").

Since the strand of 5' end protrudes by 2 bp at the end digested with BsgI, it is blunt-ended by T4 DNA polymerase treatment, for example. Further, other end digested with PmeI is a blunt end. Therefore, these ends can be ligated (FIG. 4, J). Thus, if the vector primer is cyclized by a self-ligation reaction, a vector primer having a structure comprising MAGE/pUC19 to which a short tag is ligated, in which the part of cDNA other than the tag is excised, is obtained (FIG. 4, J and K).

<4> Step (d)

Then, PCR is performed by using the vector primer cyclized in the step (c) as a template, and oligonucleotides having nucleotide sequences corresponding to respective flanking regions of the both sides of the tag in the vector primer as primers to amplify the tag.

Specifically, PCR is performed by using the vector primer containing the tag as a template, and primers corresponding to the sequences of the vector segments of the both sides of the tag (for example, those of SEQ ID NOS: 2 and 3) (FIG. 4, K). As a result, a DNA fragment containing the tag at the center is amplified (in this case, 110 bp including the sequences of primers and the tag) (FIG. 4, L).

<5> Step (e)

The aforementioned PCR amplification products are ligated to form a concatemer of the tags. At this time, if a recognition sequence for a fifth restriction enzyme that produces an end of the same shape as the end obtained by digestion with the fourth restriction enzyme is introduced into the primer for the downstream region of the tag among the primers used in the step of (d), and the amplified primer is digested with the fourth restriction enzyme and the fifth restriction enzyme, the concatemer can be formed efficiently. The type of the fifth restriction enzyme is not particularly limited. However, if the same restriction enzyme as the fourth restriction enzyme is used, the procedure will become simple. Further, the same restriction enzyme as the third restriction enzyme may be used as the fourth restriction enzyme. Furthermore, the third, fourth and fifth restriction enzymes may be the same enzyme. However, if the same enzyme is used as the fifth restriction enzyme and fourth restriction enzyme, the total sequence of the cDNA will be excised from the vector primer in the step (b). Therefore, in order to prevent this, it is necessary to introduce a nucleotide sequence different from the recognition sequence for the fifth restriction enzyme by one nucleotide at a position in a further inner position from the first restriction enzyme recognition sequence of the vector primer, and perform PCR by using a primer having a recognition sequence for the fifth restriction enzyme for the downstream side of the tag so that the nucleotide sequence different by one nucleotide is replaced with the recognition sequence for the fifth restriction enzyme. Further, when the same enzyme is used as the third restriction enzyme and fourth restriction enzyme, the recognition site of the vector primer for the fourth restriction enzyme must be made to be not digested by methylation. In this case, before digestion with the fourth restriction enzyme, the vector primer cyclized in the step (c) is introduced into the host not having the modification system for demodification.

If the ligation reaction of the tags is performed in the presence of an adaptor having one end of the same shape as an end of the tag to arrange the adaptor at each end of the concatemer, and PCR is performed by using an oligonucleotide having a sequence corresponding to the sequence of the adaptor as a primer, the concatemer can be amplified. If the adaptor is used in a smaller amount compared with the tag, or an adaptor having one end of a shape different from that of the tag, the adaptor can be arranged at each end of a concatemer consisting of a large number of tags. In this way, even a micro amount of concatemer can be cloned, and as a result, analysis becomes possible with a micro amount of sample mRNA.

The molar ratio of the tags and the adaptor is usually tag:adaptor=1:1 to 1:0.01, preferably 1:0.2 to 1:0.05. If the adaptor is used in this range, the concatemer composed of about 2 to 50 ligated tags may be obtained.

Insertion of the obtained concatemer into a cloning vector for nucleotide sequencing makes the sequencing operation easy.

Figure 5:
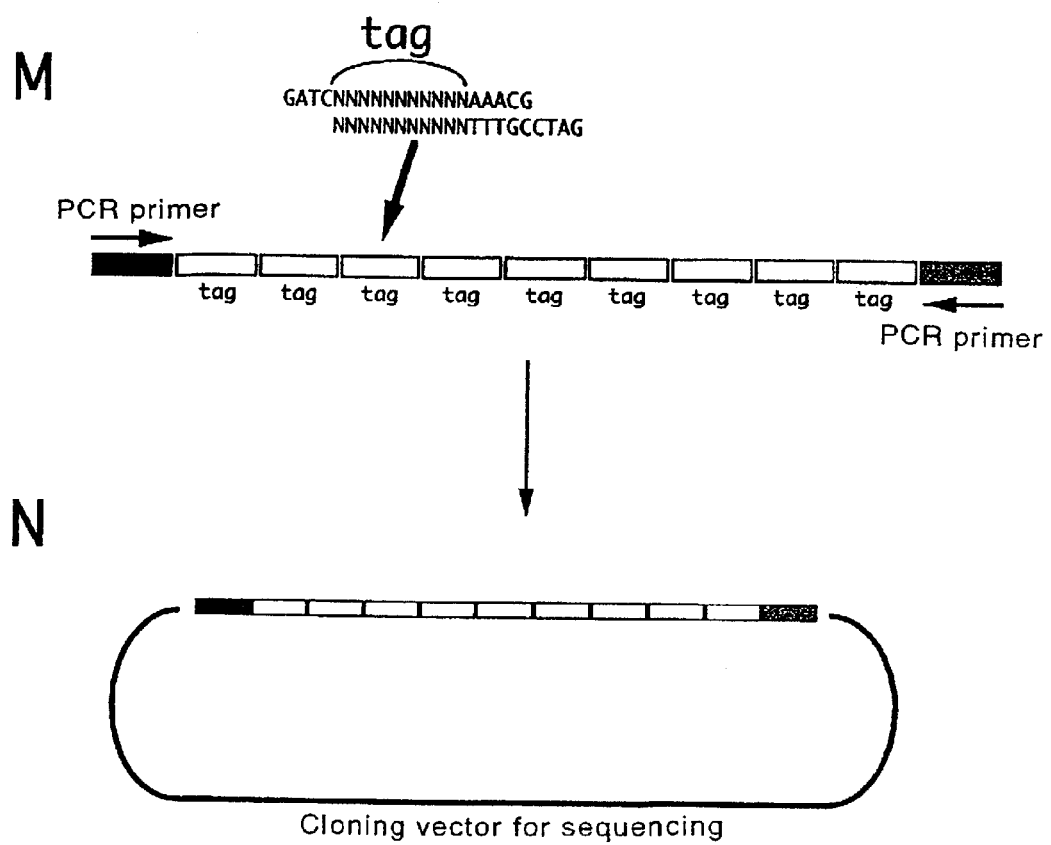
FIG. 5 schematically shows the step (e) of the method of the present invention and a step of inserting an amplification product obtained in the step (e) into a cloning vector for sequencing. The small DNA fragment (listed 5' to 3') is GATCNNNNNNNNNNNAAACG (plus strand; SEQ ID NO: 44) and GATCCGTTTNNNNNNNNNNN (minus strand; SEQ ID NO: 45).

When MAGE/pUC19 is used, a small fragment containing a tag is obtained by digesting the amplification product of the step (d) with a restriction enzyme MboI (FIG. 5, M).

The tag fragment obtained here is present between known DNA sequences, i.e., GATC and AAACG, and therefore it can definitely recognize which portion is the tag. Since MboI sites are exposed at the both ends of this tag sequence, the tags can ligated to each other by a ligation reaction to form a concatemer (FIG. 5, M).

<6> Step (f)

If the nucleotide sequence of the concatemer obtained as described above is determined, since tags derived from many cDNA molecules are contained in it, the expression frequencies of the genes from which the cDNAs originated can be analyzed by investigating types and frequencies of the tags occurring in the nucleotide sequence. Type of the tag can be determined by searching for a database containing information of partial sequences of known mRNAs (EST).

When the concatemer of the tags is amplified, two or more fragments having the same sequence will be formed. However, if a sequence considered to be the same as one previously sequenced appears in the sequence analysis after the cloning, it can be excluded from the analysis to eliminate bad influence of PCR on the genetic expression frequency analysis.

Further, when the same enzyme is used as the fourth and fifth restriction enzymes, since direction of the tags in the concatemer is not fixed, sequences of not only one strand but also the reverse strand are taken into consideration in the sequence analysis.

As explained above, in the method of the present invention, a ditag is not produced as in the SAGE method, but a tag can be prevented from directly connecting with other tags by putting each tag between known DNA fragments. As a result, the problem that the border between tags becomes indefinite is solved. Further, since a sample can be amplified by performing PCR several times, the analysis can be possible even with a micro amount of mRNA. Furthermore, the use of vector primer enables cDNA synthesis in the state that the cDNA is fused to the vector. Therefore, the analysis can be performed without using avidin and biotin beads.

EXAMPLE

Thirty five micrograms (35 μg) of mRNA was extracted from 1 g of C57BL/6 mouse livers by using Fast Track 2.0 kit produced by Invitrogen.

After cDNA was synthesized through reverse transcription by using 0.97 μg of the obtained mRNA and MAGE/pUC19, genetic expression frequency analysis was performed as follows.

The MAGE/pUC19 vector (FIG. 2, A) was digested with restriction enzymes BstXI and PstI, and the excised small fragment was removed (FIG. 2, B). Then, a partially double-stranded DNA having a single-stranded poly(T) sequence (poly(T) adaptor shown in FIG. 2, C) was ligated to the BstXI-digested end (FIG. 2, D). In this vector primer, the first restriction enzyme was PmeI, the second restriction enzyme was BglII, and the type IIS restriction enzyme was BsgI (FIG. 3, E).

Zero point two microgram (0.2 μg) of the vector primer and 0.97 μg of the mRNA derived from mouse liver were annealed, and cDNA synthesis was performed. Then a second strand was synthesized by using the synthesized first cDNA as a template (FIG. 3, F). Genetic expression frequency analysis was performed by using the obtained cDNA in an amount of 1/40 of the obtained amount of cDNA (corresponding to 0.025 μg of mRNA) as a material.

In another experiment, genetic expression frequency analysis could be successfully performed by using 0.05 μg of micro amount mRNA extracted from 4.5 mg of micro amount clinical sample as an experimental material to synthesize cDNA through reverse transcription and following the same procedures as described below.

Then, the vector primer to which the cDNA was ligated obtained as described above was digested with BglII and MboI, which were the second and third restriction enzymes, respectively (FIG. 3, G). Subsequently, the MboI end and BglII end of cDNA-MAGE/pUC19 were ligated by a self-ligation reaction to cyclize the vector primer (FIG. 3, H).

The above cyclized vector primer was digested with BsgI and PmeI, and the digested ends were blunt-ended by T4 DNA polymerase treatment. Then, the vector primer was cyclized again (FIGS. 4, I to K). PCR was performed by using this cyclized vector primer as a template, oligonucleotides having nucleotide sequences corresponding to the respective flanking regions of the both sides of the tag in the vector primer (SEQ ID NOS: 2 and 3) as primers, and an enzyme AmpliTaq Gold (PE Biosystems) to amplify the tag (FIG. 4, L). The above PCR was performed by repeating a reaction cycle of denaturation (95° C., 0.3 minute), annealing and an extension reaction with the polymerase (72° C., 1.5 minutes) for 65 cycles. As a result, a DNA fragment of 110 bp containing the tag at the center was amplified.

The above PCR amplification product was digested with MboI to excise the tag, and a ligation reaction was performed with addition of an adaptor obtained by annealing oligonucleotides having the nucleotide sequences shown in SEQ ID NOS: 4 and 5 such that the ratio of tag:adaptor should be 8:1 to form a concatemer of the tags (FIG. 5, M). This concatemer was amplified by PCR using a primer having the nucleotide sequence shown in SEQ ID NO: 6. For PCR, a reaction cycle of denaturation (95° C., 0.3 minute), annealing (40° C., 3 minutes) and an extension reaction with polymerase (72° C., 1 minute) was repeated for 5 cycles, and then a reaction cycle of denaturation (95° C., 0.3 minute), annealing and an extension reaction (72° C., 1 minute) was repeated for 60 cycles. The amplification product was digested with a restriction enzyme NotI, and inserted into the NotI site of the cloning vector pKF3 for sequencing, and the nucleotide sequence was determined.

Based on the obtained sequence data (for 11000 tags), the tags were divided into groups of tags having the same sequence, and the order of the groups according to the occurring frequency was determined. The tags ranked first to tenth for the frequency from the highest are shown in Table 1. This result shows that the gene showing the highest expression frequency in the mouse liver tissue was the urinary protein I/II gene. Following that gene, the albumin gene, the urinary protein III gene and the argininosuccinate synthase gene are ranked in the order of the expression frequency from higher one. Thus, even with a micro amount of mRNA sample, the method of the present invention shows high recovery efficiency of cDNA by the use of a vector primer, and enables genetic expression frequency analysis with high precision since ambiguity of tag sequences can be eliminated.

TABLE 1

| Tag (SEQ ID NO) | Rank for frequency | Number of tag | Designation of gene |
| --- | --- | --- | --- |
| TGCATTCCATC (7) | 1 | 2196 | Urinary protein I/II |
| CCTGGTGGAAA (8) | 2 | 1261 | Albumin |
| TGCTCTCCACC (9) | 3 | 485 | Urinary protein III |

TABLE 1-continued

| Tag (SEQ ID NO) | Rank for frequency | Number of tag | Designation of gene |
|---|---|---|---|
| GGGAAGTACGC (10) | 4 | 383 | Argininosuccinate synthase |
| ACCTCGGATGA (11) | 5 | 345 | Fibrinogen Aα |
| TTCCAGGCCCG (12) | 6 | 333 | Apolipoprotein E |
| ACCAGTGTCGC (13) | 7 | 310 | Mouse EST |
| TGCATGCCCTG (14) | 8 | 307 | Ferritin light chain |
| CACTACAGCAC (15) | 9 | 300 | Mouse EST |
| CTGCCAAGTTC (16) | 10 | 226 | Retinol-binding protein |

INDUSTRIAL APPLICABILITY

According to the present invention, expression frequencies of genes can be surely analyzed with good precision in a simple manner.

The method for analyzing genetic expression of the present invention is useful for researches concerning life science, and it is particularly useful for development of methods for treatment or diagnosis of diseases through analysis of difference in genetic expression between specific organs or cells of healthy subjects and subjects with diseases. For example, by analyzing difference in expression of genes between livers of healthy subject and subject with hepatitis by the method of the present invention, a gene of which expression is specifically increased or decreased in hepatitis can be discovered. By investigating the role in the liver of such a gene, drugs for inhibiting or accelerating the function of the gene can be developed for the purpose of treatment of hepatitis. Moreover, the gene itself, an antisense oligonucleotide designed based on the gene structure, a protein produced by expression of the gene and so forth can also be used for the treatment of hepatitis.

Further, even for a disease of which mechanism for its onset is not elucidated yet, a method of treatment may be developed by using the method of the present invention. Furthermore, if a gene of which expression is changed in a disease-specific manner can be found by the method of the present invention, it becomes possible to develop not only a method of treatment, but also a method of diagnosis of a disease.

Moreover, not only use in the medical field, the method can also be means for identifying useful genes from all of eukaryotic organisms. For example, after yeast strains suitable for the brewing of beer are bred by mutation, change of genetic expression between a parent strain and a mutant strain can be analyzed by the method of the present invention, so that a gene of which expression is changed by the mutation can be identified. By comprehensively manipulating genes advantageous for the brewing of beer, which are obtained as described above, a better brewers' yeast strain can be created.

Further, by analyzing amino acid-producing bacterial such as *Escherichia coli* and Corynebacterium bacteria, for example, more excellent amino acid-producing bacteria can be created.

What is claimed is:

1. A method for analyzing expression frequencies of genes, which comprises the following steps:
   (a) forming a vector primer to which each cDNA is ligated, by annealing the vector primer with each mRNA derived from a cell of which expression frequencies of genes is to be analyzed, and synthesizing the cDNA, said vector primer comprising a linear plasmid vector having a single-stranded poly(T) sequence at one 3' end of one strand of the linear plasmid vector, said linear plasmid vector comprising a recognition sequence for a first restriction enzyme, a recognition sequence for a type IIS restriction enzyme, and a recognition sequence for a second restriction enzyme in order from the poly(T) sequence wherein (1) the first restriction enzyme and the second restriction enzyme each digest the vector primer at one position, (2) the cleavage site of the type IIS restriction enzyme is positioned beyond the recognition sequence of the second restriction enzyme, and (3) the vector primer digested with the first restriction enzyme and the type IIS restriction enzyme can be cyclized,
   (b) digesting the vector primer to which the cDNA is ligated, with the second restriction enzyme and a third restriction enzyme that does not digest the vector primer and forms a digested end of the same shape as a digested end obtained with the second restriction enzyme, to excise an upstream region of the cDNA, and cyclizing the vector primer,
   (c) digesting the cyclized vector primer with the first restriction enzyme and the type IIS restriction enzyme to excise a downstream region of the cDNA so that a tag consisting of a part of the cDNA is left, and cyclizing the vector primer again,
   (d) performing polymerase chain reaction (PCR) by using the vector primer as a template and primers to amplify the tag, wherein said primers are oligonucleotides having nucleotide sequences corresponding to known nucleotide regions on each side of the tag that are maintained in the vector primer following digestion in step (c),
   (e) ligating the amplification products to form a concatemer of the tags, wherein the tags are separated by known nucleotide sequences introduced by the primers for tag amplification so that no ditags are present in the concatemer, and
   (f) determining the nucleotide sequence of the concatemer and investigating types and frequencies of tags occurring in the nucleotide sequence.

2. The method according to claim 1, wherein the ligation reaction in the step (e) is performed in the presence of an adaptor having one end of the same shape as an end of the tag to arrange the adaptor at each end of the concatemer, and the concatemer is amplified by performing PCR using an oligonucleotide having a sequence corresponding to the sequence of the adaptor as a primer.

3. The method according to claim 1, wherein, after the step (e), the concatemer is cloned in a cloning vector for nucleotide sequencing, and then the nucleotide sequence of the concatemer is determined.

4. The method according to claim 1, wherein the recognition sequence for the third restriction enzyme consists of four nucleotides.

5. The method according to claim 4, wherein the vector primer has a recognition sequence for a fourth restriction enzyme of which digestion point is in the same position as or a position downstream from the digestion point of the recognition sequence for the second restriction enzyme, which is not excised from the vector primer by the digestion with the type IIS restriction enzyme;
   the primer for the downstream side of the tag among the primers used in the step (d) has a recognition sequence for a fifth restriction enzyme that forms an end of the same shape as the end digested with the fourth restriction enzyme; and
   the concatemer is formed after the amplified primers are digested with the fourth restriction enzyme and the fifth restriction enzyme.

6. The method according to claim 5, wherein the vector primer has a nucleotide sequence different from the recognition sequence for the fifth restriction enzyme by one nucleotide in at a position upstream from the recognition sequence for the first restriction enzyme, and the nucleotide sequence different by one nucleotide is converted to the recognition sequence for the fifth restriction enzyme by PCR using the primer for the downstream side of the tag.

7. The method according to claim 6, wherein the third, fourth and fifth restriction enzymes are identical to one another.

8. The method according to claim 1, wherein the vector primer is formed by ligating a linear plasmid obtained by digesting a plasmid having a multicloning site at two sites in the multicloning site, and a partially double-stranded DNA having an end of the same shape as one end of the linear plasmid and a single-stranded poly(T) sequence.

9. The method according to claim 2, wherein, after the step (e), the concatemer is cloned in a cloning vector for nucleotide sequencing, and then the nucleotide sequence of the concatemer is determined.

10. The method according to claim 1, wherein said vector primer is prepared from a vector selected from the group consisting of pUC 18, pUC19, pBR322, pHSG299, pHSG298, pHSG399, pHSG398, RSF1010, pMW119, pMW118, pMW219, and pMW218.

11. The method according to claim 1, wherein said vector primer is prepared from pUC19.

12. The method according to claim 1, wherein said vector primer is prepared by cloning SEQ ID NO: 1 between EcoRI and HindIII within the multiple cloning site of a vector selected from the group consisting of pUC18, pUC19, pBR322, pHSG299, pHSG298, pHSG399, pHSG398, RSF1010, pMW119, pMW118, pMW219, and pMW218.

13. The method according to claim 1, wherein said first restriction enzyme is PmeI.

14. The method according to claim 1, wherein said second restriction enzyme is BglII.

15. The method according to claim 1, wherein said type IIS restriction enzyme is BsgI or BsmFI.

16. The method according to claim 1, wherein said single-stranded poly(T) sequence comprises 10–50 consecutive thymine nucleotides.

17. The method of claim 1, wherein said concatemer comprises 2 to 50 ligated tags.

18. The method according to claim 1, wherein at least one of said primers to amplify the tag is selected from the group consisting of SEQ ID NO:2 and SEQ ID NO:3.

19. The method according to claim 2, wherein the molar ratio of the tags to the adaptor ranges from 1:1 to 1:0.01.

20. The method according to claim 6, wherein at least one of the third, fourth and fifth restriction enzymes is MboI.

* * * * *

SEQUENCE LISTING

```
<160> NUMBER OF SEQ ID NOS: 45

<210> SEQ ID NO 1
<211> LENGTH: 47
<212> TYPE: DNA
<213> ORGANISM: Artificial Sequence
<220> FEATURE:
<223> OTHER INFORMATION: Synthetic DNA

<400> SEQUENCE: 1
gattcgtgca gatctcacac tgcagagatc caacagcatg gaagctt          47

<210> SEQ ID NO 2
<211> LENGTH: 26
<212> TYPE: DNA
<213> ORGANISM: Artificial Sequence
<220> FEATURE:
<223> OTHER INFORMATION: Synthetic DNA

<400> SEQUENCE: 2
acgccagggt tttcccagtc acgacg                                 26

<210> SEQ ID NO 3
<211> LENGTH: 39
<212> TYPE: DNA
<213> ORGANISM: Artificial Sequence
<220> FEATURE:
<223> OTHER INFORMATION: Synthetic DNA

<400> SEQUENCE: 3
atgattacgc caagcttcca tgctggctcc gatccgttt                   39
```

```
<210> SEQ ID NO 4
<211> LENGTH: 24
<212> TYPE: DNA
<213> ORGANISM: Artificial Sequence
<220> FEATURE:
<223> OTHER INFORMATION: Synthetic DNA

<400> SEQUENCE: 4
gatcgagatc tgcaaccaga gtcg                                              24

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
cgactctggt tgcagatctc                                                   20

<210> SEQ ID NO 6
<211> LENGTH: 29
<212> TYPE: DNA
<213> ORGANISM: Artificial Sequence
<220> FEATURE:
<223> OTHER INFORMATION: Synthetic DNA

<400> SEQUENCE: 6
aacttcgact gcggccgcag atctcgatc                                         29

<210> SEQ ID NO 7
<211> LENGTH: 11
<212> TYPE: DNA
<213> ORGANISM: Mus musculus

<400> SEQUENCE: 7
tgcattccat c                                                            11

<210> SEQ ID NO 8
<211> LENGTH: 11
<212> TYPE: DNA
<213> ORGANISM: Mus musculus

<400> SEQUENCE: 8
cctggtggaa a                                                            11

<210> SEQ ID NO 9
<211> LENGTH: 11
<212> TYPE: DNA
<213> ORGANISM: Mus musculus

<400> SEQUENCE: 9
tgctctccac c                                                            11

<210> SEQ ID NO 10
<211> LENGTH: 11
<212> TYPE: DNA
<213> ORGANISM: Mus musculus

<400> SEQUENCE: 10
gggaagtacg c                                                            11

<210> SEQ ID NO 11
<211> LENGTH: 11
```

-continued

```
<212> TYPE: DNA
<213> ORGANISM: Mus musculus

<400> SEQUENCE: 11
acctcggatg a                                                        11

<210> SEQ ID NO 12
<211> LENGTH: 11
<212> TYPE: DNA
<213> ORGANISM: Mus musculus

<400> SEQUENCE: 12
ttccaggccc g                                                        11

<210> SEQ ID NO 13
<211> LENGTH: 11
<212> TYPE: DNA
<213> ORGANISM: Mus musculus

<400> SEQUENCE: 13
accagtgtcg c                                                        11

<210> SEQ ID NO 14
<211> LENGTH: 11
<212> TYPE: DNA
<213> ORGANISM: Mus musculus

<400> SEQUENCE: 14
tgcatgccct g                                                        11

<210> SEQ ID NO 15
<211> LENGTH: 11
<212> TYPE: DNA
<213> ORGANISM: Mus musculus

<400> SEQUENCE: 15
cactacagca c                                                        11

<210> SEQ ID NO 16
<211> LENGTH: 11
<212> TYPE: DNA
<213> ORGANISM: Mus musculus

<400> SEQUENCE: 16
ctgccaagtt c                                                        11

<210> SEQ ID NO 17
<211> LENGTH: 48
<212> TYPE: DNA
<213> ORGANISM: Artificial Sequence
<220> FEATURE:
<223> OTHER INFORMATION: Synthetic DNA

<400> SEQUENCE: 17
aagcttccat gctgttggat ctctgcagtg tgagatctgc acgaattc                48

<210> SEQ ID NO 18
<211> LENGTH: 25
<212> TYPE: DNA
<213> ORGANISM: Artificial Sequence
<220> FEATURE:
<223> OTHER INFORMATION: Synthetic DNA

<400> SEQUENCE: 18
```

-continued

```
gaattcgtgc agatctcaca ctgca                                    25

<210> SEQ ID NO 19
<211> LENGTH: 13
<212> TYPE: DNA
<213> ORGANISM: Artificial Sequence
<220> FEATURE:
<223> OTHER INFORMATION: Synthetic DNA

<400> SEQUENCE: 19
gagatccaac agc                                                 13

<210> SEQ ID NO 20
<211> LENGTH: 10
<212> TYPE: DNA
<213> ORGANISM: Artificial Sequence
<220> FEATURE:
<223> OTHER INFORMATION: Synthetic DNA

<400> SEQUENCE: 20
atggaagctt                                                     10

<210> SEQ ID NO 21
<211> LENGTH: 21
<212> TYPE: DNA
<213> ORGANISM: Artificial Sequence
<220> FEATURE:
<223> OTHER INFORMATION: Synthetic DNA

<400> SEQUENCE: 21
gtgtgagatc tgcacgaatt c                                        21

<210> SEQ ID NO 22
<211> LENGTH: 13
<212> TYPE: DNA
<213> ORGANISM: Artificial Sequence
<220> FEATURE:
<223> OTHER INFORMATION: Synthetic DNA

<400> SEQUENCE: 22
ttggatctct gca                                                 13

<210> SEQ ID NO 23
<211> LENGTH: 14
<212> TYPE: DNA
<213> ORGANISM: Artificial Sequence
<220> FEATURE:
<223> OTHER INFORMATION: Synthetic DNA

<400> SEQUENCE: 23
aagcttccat gctg                                                14

<210> SEQ ID NO 24
<211> LENGTH: 26
<212> TYPE: DNA
<213> ORGANISM: Artificial Sequence
<220> FEATURE:
<223> OTHER INFORMATION: Synthetic DNA

<400> SEQUENCE: 24
cggagtttaa acggattgga gccagc                                   26

<210> SEQ ID NO 25
<211> LENGTH: 62
<212> TYPE: DNA
<213> ORGANISM: Artificial Sequence
```

```
<220> FEATURE:
<223> OTHER INFORMATION: Synthetic DNA

<400> SEQUENCE: 25
gctccaatcc gtttaaactc cgttttttt tttttttttt tttttttttt         60
tt                                                            62

<210> SEQ ID NO 26
<211> LENGTH: 36
<212> TYPE: DNA
<213> ORGANISM: Artificial Sequence
<220> FEATURE:
<223> OTHER INFORMATION: Synthetic DNA

<400> SEQUENCE: 26
cggagtttaa acggattgga gccagcatgg aagctt                       36

<210> SEQ ID NO 27
<211> LENGTH: 76
<212> TYPE: DNA
<213> ORGANISM: Artificial Sequence
<220> FEATURE:
<223> OTHER INFORMATION: Synthetic DNA

<400> SEQUENCE: 27
aagcttccat gctggctcca atccgtttaa actccgtttt tttttttttt tttttttttt    60
tttttttttt tttttt                                                    76

<210> SEQ ID NO 28
<211> LENGTH: 24
<212> TYPE: DNA
<213> ORGANISM: Artificial Sequence
<220> FEATURE:
<223> OTHER INFORMATION: Synthetic DNA
<220> FEATURE:
<221> NAME/KEY: polyA_signal
<222> LOCATION: (1)..(24)
<223> OTHER INFORMATION:

<400> SEQUENCE: 28
aaaaaaaaaa aaaaaaaaaa aaaa                                    24

<210> SEQ ID NO 29
<211> LENGTH: 66
<212> TYPE: DNA
<213> ORGANISM: Artificial Sequence
<220> FEATURE:
<223> OTHER INFORMATION: Synthetic DNA

<400> SEQUENCE: 29
aagcttccat gctggctcca atccgtttaa actccgtttt tttttttttt tttttttttt    60
tttttt                                                               66

<210> SEQ ID NO 30
<211> LENGTH: 104
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(48)
<223> OTHER INFORMATION: n = a, c, g, or t

<400> SEQUENCE: 30
```

```
nnnnnnnnnn nnnnnnnnnn nnnnnnnnnn nnnnnnnnnn nnnnnnnnaa aaaaaaaaaa    60
aaaaaaaacg gagtttaaac ggattggagc cagcatggaa gctt                      104

<210> SEQ ID NO 31
<211> LENGTH: 104
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (57)..(104)
<223> OTHER INFORMATION: n = a, c, g, or t

<400> SEQUENCE: 31
aagcttccat gctggctcca atccgtttaa actccgtttt ttttttttt tttttnnnn      60 nnnnnnnnnn nnnnnnnnnn nnnnnnnnnn nnnnnnnnnn nnnn                    104

<210> SEQ ID NO 32
<211> LENGTH: 96
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (16)..(45)
<223> OTHER INFORMATION: n = a, c, g, or t

<400> SEQUENCE: 32
gaattcgtgc agatcnnnnn nnnnnnnnnn nnnnnnnnnn nnnnnaaaa aaaaaaaaa      60 cggagtttaa acggattgga gccagcatgg aagctt                              96

<210> SEQ ID NO 33
<211> LENGTH: 96
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (52)..(81)
<223> OTHER INFORMATION: n = a, c, g, or t

<400> SEQUENCE: 33
aagcttccat gctggctcca atccgtttaa actccgtttt tttttttttt tnnnnnnnnn    60
nnnnnnnnnn nnnnnnnnnn ngatctgcac gaattc                              96

<210> SEQ ID NO 34
<211> LENGTH: 28
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (16)..(28)
<223> OTHER INFORMATION: n = a, c, g, or t

<400> SEQUENCE: 34
gaattcgtgc agatcnnnnn nnnnnnnn                                       28

<210> SEQ ID NO 35
<211> LENGTH: 40
<212> TYPE: DNA
<213> ORGANISM: Artificial Sequence
```

```
<220> FEATURE:
<223> OTHER INFORMATION: Synthetic DNA
<220> FEATURE:
<221> NAME/KEY: misc_feature
<222> LOCATION: (1)..(17)
<223> OTHER INFORMATION: n = a, c, g, or t

<400> SEQUENCE: 35
nnnnnnnnnn nnnnnnnaaa aaaaaaaaaa aacggagttt                          40

<210> SEQ ID NO 36
<211> LENGTH: 28
<212> TYPE: DNA
<213> ORGANISM: Artificial Sequence
<220> FEATURE:
<223> OTHER INFORMATION: Synthetic DNA

<400> SEQUENCE: 36
aaacggattg gagccagcat ggaagctt                                       28

<210> SEQ ID NO 37
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(11)
<223> OTHER INFORMATION: n = a, c, g, or t

<400> SEQUENCE: 37
nnnnnnnnnn ngatctgcac gaattc                                         26

<210> SEQ ID NO 38
<211> LENGTH: 42
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (24)..(42)
<223> OTHER INFORMATION: n = a, c, g, or t

<400> SEQUENCE: 38
aaactccgtt tttttttttt tttnnnnnnn nnnnnnnnnn nn                       42

<210> SEQ ID NO 39
<211> LENGTH: 28
<212> TYPE: DNA
<213> ORGANISM: Artificial Sequence
<220> FEATURE:
<223> OTHER INFORMATION: Synthetic DNA

<400> SEQUENCE: 39
aagcttccat gctggctcca atccgttt                                       28

<210> SEQ ID NO 40
<211> LENGTH: 54
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (16)..(26)
<223> OTHER INFORMATION: n = a, c, g, or t
```

```
<400> SEQUENCE: 40
gaattcgtgc agatcnnnnn nnnnnnaaac ggattggagc cagcatggaa gctt            54

<210> SEQ ID NO 41
<211> LENGTH: 54
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (29)..(39)
<223> OTHER INFORMATION: n = a, c, g, or t

<400> SEQUENCE: 41
aagcttccat gctggctcca atccgttttn nnnnnnnng atctgcacga attc             54

<210> SEQ ID NO 42
<211> LENGTH: 24
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (5)..(15)
<223> OTHER INFORMATION: n = a, c, g, or t

<400> SEQUENCE: 42
gatcnnnnnn nnnnnaaacg gatc                                             24

<210> SEQ ID NO 43
<211> LENGTH: 24
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (10)..(20)
<223> OTHER INFORMATION: n = a, c, g, or t

<400> SEQUENCE: 43
gatccgtttn nnnnnnnnn gatc                                              24

<210> SEQ ID NO 44
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (5)..(15)
<223> OTHER INFORMATION: n = a, c, g, or t

<400> SEQUENCE: 44
gatcnnnnnn nnnnnaaacg                                                  20

<210> SEQ ID NO 45
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
```

-continued

```
<222> LOCATION: (10)..(20)
<223> OTHER INFORMATION: n = a, c, g, or t

<400> SEQUENCE: 45
gatccgtttn nnnnnnnnnn                                              20
```